US008828439B2

(12) United States Patent
Kuznicki

(10) Patent No.: US 8,828,439 B2
(45) Date of Patent: Sep. 9, 2014

(54) TITANOSILICATE MOLECULAR SIEVE SUPPORTED METALLIC NANODOTS AND METHODS OF USE TO ADSORB NOBLE GASES

(75) Inventor: Steven Kuznicki, Edmonton (CA)

(73) Assignee: The Governors of the University of Alberta, Edmonton, Alberta (CA)

(*) Notice: Subject to any disclaimer, the term of this patent is extended or adjusted under 35 U.S.C. 154(b) by 0 days.

(21) Appl. No.: 13/401,145

(22) Filed: Feb. 21, 2012

(65) Prior Publication Data

US 2012/0144999 A1 Jun. 14, 2012

Related U.S. Application Data

(62) Division of application No. 12/272,366, filed on Nov. 17, 2008, now abandoned.

(60) Provisional application No. 60/988,289, filed on Nov. 15, 2007.

(51) Int. Cl.
*A61K 9/14* (2006.01)

(52) U.S. Cl.
USPC .............................. 424/489; 977/773; 95/127

(58) Field of Classification Search
CPC .... B01D 53/02; B01D 53/04; B01D 2253/10; B01D 2257/112; B01J 20/0211; B01J 20/32; B82Y 30/00; C01P 2004/64; F25J 3/04745; F25J 2205/60; F25J 2215/34; F25J 2215/36
See application file for complete search history.

(56) References Cited

U.S. PATENT DOCUMENTS

| | | | |
|---|---|---|---|
| 3,013,985 A | 12/1961 | Breck et al. | |
| 3,033,982 A | 12/1961 | Breck et al. | |
| 3,200,082 A | 8/1965 | Breck et al. | |
| 3,248,170 A | 4/1966 | Kvetinskas | |
| 4,673,559 A | 6/1987 | Derouane et al. | |
| 4,744,805 A | 5/1988 | Maroulis et al. | |
| 4,747,854 A | 5/1988 | Maroulis et al. | |
| 4,874,525 A | 10/1989 | Markovs | |
| 4,874,592 A | 10/1989 | Shino et al. | |
| 5,069,698 A | 12/1991 | Cheung et al. | |
| 5,071,804 A | 12/1991 | Kuznicki et al. | |
| 5,122,173 A | 6/1992 | Agrawal et al. | |
| 5,223,022 A | 6/1993 | Kuznicki et al. | |
| 5,226,933 A | 7/1993 | Knaebel et al. | |
| 5,470,378 A | 11/1995 | Kandybin et al. | |
| 5,837,275 A | 11/1998 | Burrell et al. | |
| 5,916,836 A | 6/1999 | Toufar et al. | |
| 6,168,649 B1 | 1/2001 | Jensvold et al. | |
| 6,432,170 B1 | 8/2002 | Chiang et al. | |
| 6,544,318 B2 | 4/2003 | Dee et al. | |
| 6,572,838 B1 | 6/2003 | Sebastian et al. | |
| 6,953,494 B2 | 10/2005 | Nelson, Jr. | |
| 7,455,718 B2 | 11/2008 | Ackley et al. | |
| 2003/0106335 A1* | 6/2003 | Golden et al. | ................... 62/648 |
| 2005/0203237 A1 | 9/2005 | Dekkers et al. | |
| 2006/0008442 A1 | 1/2006 | MacDonald et al. | |
| 2007/0087934 A1* | 4/2007 | Martens et al. | ................ 502/214 |
| 2009/0202655 A1 | 8/2009 | Kuznicki | |
| 2010/0021559 A1 | 1/2010 | Kuznicki | |
| 2010/0050868 A1 | 3/2010 | Kuznicki et al. | |

FOREIGN PATENT DOCUMENTS

| | | |
|---|---|---|
| CA | 2563727 | 9/2005 |
| EP | 1604953 | 12/2005 |
| WO | 9104096 | 4/1991 |
| WO | 9621745 | 7/1996 |
| WO | 2005087855 | 9/2005 |
| WO | 2008070988 | 6/2008 |

OTHER PUBLICATIONS

Kuznicki SM, et al. 2007. Xenon Adsorption on Modified ETS-10. J. Phys. Chem Lett.: 111: 1560-1562. (published Jan. 4, 2007).*
Barrer, R.M. et al.; Mercury Uptake in Cationic Forms of Several Zeolites; Journal of the Chemical Society; 1967; pp. 19-25; Section A, Inorganic, Physical, and Theoretical Chemistry, Part 1; London: The Chemical Society.
Jin, R. et al.; Controlling Anisotropic Nanoparticle Growth Through Plasmon Excitation; Nature; 2003; vol. 425; pp. 487-490; Nature Publishing Group.
Jin, R. et al.; Photoinduced Conversion of Siver Nanospheres to Nanoprisms; Science; 2001; vol. 294; pp. 1901-1903.
Callegari, A. et al.; Photochemically Grown Silver Nanoparticles with Wavelength-Controlled Size and Shape; Nano Letters; 2003; vol. 3, No. 11; pp. 1565-1568; American Chemical Society.
Sun, Y et al.; Transformation of Siver Nanosperes into Nanobelts and Triangular Nanoplates Through a Thermal Process; Nano Letters; 2003; vol. 3, No. 5; pp. 675-679; American Chemical Society.
Xia, Y. et al.; One-Dimensional Nanostructures: Synthesis, Characterization, and Applications; Advanced Materials; 2003; vol. 15, No. 5; pp. 353-389; Wiley-Vch Verlag GmbH & Co.
Chen, S. et al.; Synthesis and Charcterization of Truncated Triangular Silver Nanoplates; Nano Letters; 2002; vol. 2, No. 9; pp. 1003-1007; American Chemical Society.

(Continued)

*Primary Examiner* — Carlos Azpuru
*Assistant Examiner* — David Browe
(74) *Attorney, Agent, or Firm* — Bennett Jones LLP

(57) ABSTRACT

A metal nanodot material is formed by ion-exchange with an ETS zeolite, followed by activation to form metallic nanodots. The nanodot may be formed from silver, nickel, copper, gold or a platinum group metal.

16 Claims, 7 Drawing Sheets

(56) References Cited

OTHER PUBLICATIONS

Zhou, Y. et al.; A Novel Ultraviolet Irradiation Technique for Shape-Controlled Synthesis of Gold Nanoparticles at Room Temperature; Chemical Materials; 1999; vol. 11; pp. 2310-2312; American Chemical Society.

Edmondson, M.J. et al.; Electron-Beam Induced Growth of Bare Silver Nanowires from Zeolite Crystallites; Advanced Materials; 2001; vol. 13, No. 21; pp. 1608-1611; Wiley-Vch Verlag GmbH & Co.

Li, C. et al.; In Situ Observation of Bamboo-Shoot-Like One-Dimensional Growth of SiOx-AgyO Nanowires Induced by Electron Beam Irradiation; Materials Letters; 2004; vol. 58; pp. 3573-3577; Science Direct.

Worboys, L.M. et al.; Silver Nanowires: Inclusion in and Extrusion from Mesoporous Supports; Studies in Surface Science and Catalysis; 2004; vol. 154; pp. 931-938; Elsevier B.V.

Tsapatsis, M.; Molecular Sieves in the Nanotechnology Era; Perspective; 2002; vol. 48, No. 4; pp. 654-660; American Institute of Chemical Engineers.

Strohal, R. et al.; Nanocrystalline Silver Dressings as an Efficient Anti-MRSA Barrier: A New Solution to an Increasing Problem; Science Direct; Journal of Hospital Infection; 2005; vol. 60; pp. 226-230; Elsevier Ltd.

Metraux, G.S. et al.; Rapid Thermal Synthesis of Silver Nanoprisms with Chemically Tailorable Thickness; Advanced Materials; 2005; vol. 17, No. 4; pp. 412-415; Wiley-Vch Verlag GmbH & Co.

Gellens, L.R. et al.; Oxidation and Reduction of Silver in Zeolite Y: A Structural Study; Zeolites; 1981; vol. 1; pp. 85-90; IPC Business Press.

Gurin, V.S. et al.; Metal Clusters and Nanoparticles Assembled in Zeolites: An Example of Stable Materials with Controllable Particle Size; Materials Science & Engineering; 2002; vol. 19; pp. 327-331; Elsevier Science B.V.

Gurin, V.S. et al.; Silver and Copper Nanostructures Within the Erionite Regular Lattice: Interplay Between Intra- and Extra-Crystalline Location; Materials & Science Engineering; 2003; vol. C23; pp. 81-85; Elsevier Science B.V.

Gurin, V.S. et al.; Silver and Copper Clusters and Small Particles Stabilized Within Nanoporous Silicate-Based Materials; Materials Science & Engineering; 2005; vol. A 391; pp. 71-76; Elsevier B.V.

Bagnasco, G. et al.; Oxidation of Ethylene on Silver-Loaded Natural Zeolites; 1982; pp. 275-283; Elsevier.

Cho, S.J. et al.; Effect of Multivalent Cations on Agglomeration of Ru Clusters Supported on Y Zeolite; Catalysis; 2000; vol. 71, No. 3-4; Plenum Publishing Corporation.

Alt, V. et al.; An In Vitro Assessment of the Antibacterial Properties and Cytotoxicity of Nanoparticulate Silver Bone Cement; Biomaterials; 2005; vol. 25; pp. 4383-4391; Elsevier Ltd.

Anderson, M.W. et al.; Structure of the Microporous Titanosilicate ETS-10; Letters to Nature; 1994; vol. 367, No. 27; pp. 347-351; Nature Publishing Group.

Anderson, M.W. et al.; Microporous Titansilicate ETS-10: A Structural Survey; Philosophical Magazine B; 1995; vol. 71, No. 5; pp. 813-841; Taylor & Francis Ltd.

Sankar, G. et al.; Determination of the Structure of Distorted TIO6 Units in the Titanoisilicate ETS-10 by a Combination of X-ray Absorption Spectroscopy and Computer Modeling; J. Phys. Chem.; 1996; vol. 100; pp. 449-452; American Chemical Society.

Sun, T. et al.; Silver Clusters and Chemistry in Zeolites; Chemical Reviews; 1994; vol. 94, No. 4; pp. 857-870; American Chemical Society.

Hutson N.D. et al.; Silver Ion-Exchanged Zeolites Y, X, and Low-Silica X: Observations of Thermally Induced Cation/Cluster Migration and the Resulting Effects on the Equilibrium Absorption of Nitrogen; Chemical Matters; 2000; vol. 12, No. 10; pp. 3020-3031; American Chemical Society.

Sebastian, J. et al.; Sorption of Nitrogen, Oxygen, and Argon in Silver-Exchanged Zeolites; Ind. Eng. Chem. Res.; 2005; vol. 44, No. 21; pp. 8014-8024; American Chemical Society.

Grosse, R. et al.; 129Xe NMR of Silver-Exchanged X- and Y-Type Zeolites; J. Phys. Chem.; 1991; vol. 95, No. 6; pp. 2443-2447; American Chemical Society.

Grosse, R. et al.; Absorption and 129 Xe n.m.r. of Xenon in Silver-Exchanged Y Zeolites: Application to the Location of Silver Cations; Zeolites; 1992; vol. 12; pp. 909-915; Butterworth-Heinemann.

Watermann, J. et al.; Isoteric Heats of Adsorption of Xenon in Silver-Exchanged Y Zeolites; Zeolites; 1993; vol. 13; pp. 427-429; Butterworth-Heinemann.

Munakata, K. et al.; Absorption of Noble Gases on Silver-Mordenite; Journal of Nuclear Science and Technology; vol. 40, No. 9; pp. 695-697.

Lynch, C. et al.; Xenon Anesthesia; Clinical Concepts and Commentary; 2000; vol. 92, No. 3; Anesthesiology.

Hammarlund, N.; The Krypton and Xenon Markets Up to the Year 2000; Nuclear Instruments & Methods in Physics Research; 1992; vol. A316; pp. 83-87; Elsevier Science Publishers B.V.

Lard, E.W. et al.; Separation and Determination of Argon, Oxygen, and Nitrogen by Gas Chromatography; Analytical Chemistry; 1960; vol. 32, No. 7; pp. 878-879.

Jones, K. et al.; Separation and Determination of Argon and Oxygen in High-Purity Nitrogen Streams by Gas Chromatography; Nature; 1964; vol. 202, No. 4936; pp. 1003-1004; Nature Publishing Group.

Walker, J.A.J. et al.; Chromatographic Separation of Argon and Oxygen Using Molecular Sieve; 1966; No. 5019; pp. 197; Nature Publishing Group.

Pollock, G.E. et al.; Gas Chromatographic Separation of Nitrogen, Oxygen, Argon, and Carbon Monoxide Using Custom-Made Porous Polymers from High Purity Divinylbenzene; Journal of Chromatographic Science; 1984; vol. 22; pp. 343-347.

Pollock, G.E.; Synthesis of a Further Improved Porous Polymer for the Separation of Nitrogen, Oxygen, Argon, and Carbon Monoxide by Gas Chromatography; Technical Note; 1986; vol. 24; pp. 173-174; Journal of Chromatographic Science.

Maroulis,. P.J. et al.; Calcium Chabazite Adsorbent for the Gas Chromatographic Separation of Trace Argon-Oxygen Mixtures; Anal. Chem.; 1989; vol. 61; pp. 1112-1117; American Chemical Society.

Rege, S.U. et al.; Kinetic Separation of Oxygen and Argon Using Molecular Siece Carbon; Adsorption; vol. 6; pp. 15-22; Kluwer Academic Publishers.

Jin, X. et al.; Production of Argon from an Oxygen-Argon Mixture by Pressure Swing Adsorption; Ind. Eng. Chem. Res.; 2006; vol. 45, No. 16; pp. 5775-5787; American Chemical Society.

Sebastian, J. et al.; Anomalous Adsorption of Nitrogen and Argon in Silver Exchanged Zeolite A; ChemComm; 2003; pp. 268-269; The Royal Society of Chemistry.

Yang, R.T. et al.; Zeolites Containing Mixed Cations for Air Separation by Weak Chemisorption-Assisted Adsorption; Ind. Eng. Chem. Res.; 1996; vol. 35, No. 9; pp. 3093-3099; American Chemical Society.

Dewar, M.J.S.; A Review of the Complex Theory; Colloque International de Montpellier; 1951; vol. C71.

Hutson, N.D. et al.; Mixed Cation Zeolites: Lix Agy -X as a Superior Adsorbent for Air Separation; Separations; 1999; vol. 45, No. 4; pp. 724-734; American Institute of Chemical Engineers.

Salla, I. et al.; Study of the Influence of Several Mordenite Modifications on Its N2 and O2 Adsorption Properties; J. Phys. Chem.; 2004; vol. 108; pp. 5359-5364; American Chemical Society.

Diaz, E. et al.; Evaluation of Adsorption Properties of Zeolites Using Inverse Gas Chromatography: Comparison With Immersion Calorimetry; Thermochimica Acta; 2005; vol. 434; pp. 9-14; Elsevier B.V.

Zangwill, A.; Thermodynamics; Physics at Surfaces; 1988; pp. 192-194; Cambridge University Press.

Huheey, J.E.; Bond Energies and Bond Lengths; Inorganic Chemistry, 3rd Ed.; 1983; Appendix E; pp. A-28-A-44; Harper & Row.

Kuznicki, S.M. et al.; Metal Nanodots Formed and Supported on Chabazite and Chbazite-Like Surfaces; Microporous and Mesoporous Materials; 2007; vol. 103; pp. 309-315; Elsevier Inc.

Durham, M.D. et al.; Field Test Program to Develop Comprehensive Design, Operating and Cost Data for Mercury Control Systems on

(56) References Cited

OTHER PUBLICATIONS

Non-Scrubbed Coal-Fired Boilers; Air & Waste Management Association 84th Annual Meeting and Exhibition; 2001; Orlando, Florida, USA.

Erickson, B.E.; Regnerating Mercury-Loaded Sorbents; Environmental Science & Technology; 2002; pp. 408A-409A; American Chemical Society.

Granite, E.J. et al.; Novel Sorbents for Mercury Removal from Flue Gas; Ind. Chem. Res.; 2000; vol. 39; pp. 1020-1029; American Chemical Society.

Hall, B. et al.; Chemical Reactions of Mercury in Combustion Flue Gases; Water, Air and Soil Pollution; 1991; vol. 56; pp. 3-14; Kluwer Academic Publishers.

Hayhurst, D.T.; The Potential of Use of Natural Zeolites for Ammonia Removal During Coal-Gasification; Natural Zeolites: Occurrence; 1978; pp. 503-507; Use Permagon Press.

Holmes, M. et al.; Mercury Information Clearinghouse: Quarterly 1—Sorbent Injection Technologies for Mercury Control; U.S.D.O.E.#DE-FC26-98FT40321; 21 pages; http://www.ceamercuryprogram.ca.

Lewis, L.N.; Chemical Catalysis by Colloids and Clusters; Chemical Review; 1993; vol. 93; pp. 2693-2730; America Chemical Society.

Massalski, T.B.; Binary Alloy Phase Diagrams; ASM International, Materials Park; 1990; vol. 1; pp. 43-45; Ohio.

Miller, S.J. et al.; Flue Gas Effects on a Carbon-Based Mercury Sorbent; Fuel Processing Technology; 2000; vol. 65-66; pp. 343-363; Elsevier Science.

Miller, B.G.; Pollutants with Pending Compliance Regulation; Coal Energy Systems; 2005; pp. 369-373; Elsevier.

Mondale, K.D. et al.; the Comparative Ion Exchange Capacities of Natural Sedimentary and Synthetic Zeolites; Minerals Engineering; 1995; vol. 8, No. 4/5; pp. 535-548; Elsevier Science Ltd.

Morris, T. et al.; The Effects of Mercury Adsorption on the Optical Response of Size-Selected Gold and Silver Nanoparticles; Langmuir; 2002; vol. 18; pp. 7261-7264; American Chemical Society.

Mottet, C. et al; Single Impurity Effect on the Melting of Nanoclusters; Physical Review Letters; 2005; vol. 95; pp. 035501-1-035501-4; The American Physical Society.

Nelson, S. Jr. et al.; Accumulated Power-Plant Mercury-Removal Experience with Brominated PAC Injection; Combined Power Plant Air Pollutant Control Mega Symposium; 2004; Washington, DC, USA.

Pawlow, P. Uber die Abhangigkeit des Schmelzpunktes von der Oberflachenenergie eines festen Korpers; Z. Phys. Chem; 1909; vol. 65; pp. 10-35.

Pavlish, J.H. et al.; Technical Review of Mercury Technology Options for Canadian Utilities—A Report to the Canadian Council of Ministers of the Environment; Final Report for the Canadian Council of Ministers of the Environment; 2005; 22 pages; Winnipeg, Manitoba, Canada.

Seidel, A. et al.; Copper Nanoparticles in Zeolite Y; Journal of Materials Chemistry; 1999; vol. 9; pp. 2495-2498; J. Mater. Chem.

Senior, C.L.; Impact of Carbon-in-Ash on Mercury Removal Across Particulate Control Devices in Coal-Fired Power Plants; Energy & Fuels; 2005; vol. 19; pp. 859-863; American Chemical Society.

Shvartsburg, A.A. et al.; Solid Clusters Above the Bulk Melting Point; Physical Review Letters; 2000; vol. 85, No. 12; pp. 2530-2532; The American Physical Society.

Sobral, L.G.S. et al.; Electrolytic Treatment of Mercury-Loaded Activated carbon From a Gas Cleaning System; The Science of the Total Environment; 2000; vol. 261; pp. 195-201; Elsevier Science B.V.

Vidic, R.D. et al.; Vapor-Phase Elemental Mercury Adsorption by Activated Carbon Impregnated with Chloride and Chelating Agents; Carbon; 2001; vol. 39; pp. 3-14; Elsevier Science Ltd.

GSA Resources, Inc.; www.gsaresources.com.

Baerlocher, Ch. et al.; Altas of Zeolite Framework Types; 2001; 5th rev. ed.; Amsterdam; Elsevier.

Hall, Bjorn et al.; Mercury Chemistry in Simulated Flue Gases Related to Waste Incineration Conditions; Environ. Sci. Telchnol.; 1990; vol. 24, No. 1; pp. 108-111; American Chemical Society.

Thrush, Kathleen A., et al.; Characterization of Chabazite and Chabazite-like Zeolites of Unusual Compositions; J. Chem. Soc.; 1991; vol. 87(7); pp. 1031-1035; Royal Society of Chemistry.

Breck, D.W.; Zeolite Molecular Sieves; 1974; pp. 31-32; John Wiley; New York.

\* cited by examiner 20 nm

TITANOSILICATE MOLECULAR SIEVE SUPPORTED METALLIC NANODOTS AND METHODS OF USE TO ADSORB NOBLE GASES

CROSS REFERENCE TO RELATED APPLICATION

This application is a divisional application of U.S. patent application Ser. No. 12/272,366 entitled "Titanosilicate Molecular Sieve Supported Metallic Nanodots and Methods of Use to Adsorb Noble Gases, filed on Nov. 17, 2008 which claimed the priority benefit of U.S. Provisional Application No. 60/988,289 filed on Nov. 15, 2007 entitled "Zeolite Supported Metallic Nanodots", the contents of both which are incorporated herein by reference.

FIELD OF THE INVENTION

The present invention relates to metal nanodots formed on titanosilicate zeolitic materials and to methods of noble gas adsorption using such supported metal nanodots.

BACKGROUND

Metal nanoparticles and nanowires are the subject of current research efforts motivated by their high potential utility derived from nanoscale induced optical, electrical and chemical properties.

A wide range of techniques has been reported to synthesize metal nanoparticles including numerous high vacuum approaches as well as a range of photochemical [1-3] and thermal methods [4-7]. A technique that is just beginning to gain attention is the potential use of zeolite surfaces to induce the growth of metal nanostructures [8-10]. With many of their properties manifested on a nano- and subnano-dimensional scale, molecular sieves would appear to be excellent candidates to be in the vanguard of such nanofabrication efforts [11].

Unfortunately, current techniques for the generation of metal nanoparticles, such as nanosilver, are expensive and cumbersome [14]. Sub-nanometer silver ensembles can be induced to form within zeolite cavities under certain conditions [15-18], and much larger configurations often form on zeolite surfaces under reductive atmospheres. While metals readily congregate on zeolite surfaces, achieving stable, zeolite supported metal nanoscale structures has proved difficult because of the high metal mobility generally seen on zeolite surfaces. Typically, upon reduction, metals ion-exchanged into zeolite crystals diffuse to the crystal surface and rapidly coalesce into micron-scale agglomerates [19, 20]. Because of the low surface to volume ratio of these agglomerates (compared to nanometal ensembles), they generally behave like bulk metals, not displaying the novel properties anticipated for nanoparticulates.

Nanoparticulate silver has many potential uses. Many useful properties might be expected if inexpensive nanostructured silver materials were readily available. Silver is a well-known antimicrobial agent and nanoscale silver is finding increasing usage in medical devices, bandages and related medical applications [12, 13]. Current methods to generate nanosilver center on complex techniques such as surface sputtering. Research level work in biomedical engineering implants is showing promise in nanosilver bone cements where nanoparticle size control ranges from 5 nm to 50 nm [21].

Powerful surface plasmon absorption of nanoparticulate silver makes them particularly useful in applications such as biosensors, for example. Silver nanodots may be photo-fluorescence markers, which make them useful for a number of medical and similar applications. They are environmentally and biologically benign. Other exemplary silver nanodot applications include smart windows, rewritable electronic paper, electronic panel displays, memory components, and others.

A wide range of techniques has been reported to synthesize metal nanodots. Silver nanodots and their formation have recently been discussed by Metraux and Mirkin, 2005 [14]. Traditional methods for the production of silver nanodots require use of potentially harmful chemicals such as hydrazine, sodium borohydride and dimethyl formamide ("DMF"). These chemicals pose handling, storage, and transportation risks that add substantial cost and difficulty to the production of silver nanodots. A highly trained production workforce is required, along with costly production facilities outfitted for use with these potentially harmful chemicals.

Another disadvantage of known methods for producing silver nanodots relates to the time and heat required for their production. Known methods of production utilize generally slow kinetics, with the result that reactions take a long period of time. The length of time required may be shortened by some amount by applying heat, but this adds energy costs, equipment needs, and otherwise complicates the process. Known methods generally require reaction for 20 or more hours at elevated temperatures of 60° to 80° C., for example. The relatively slow kinetics of known reactions also results in an undesirably large particle size distribution and relatively low conversion. The multiple stages of production, long reaction times at elevated temperatures, relatively low conversion, and high particle size distribution of known methods make them costly and cumbersome, particularly when practiced on a commercial scale.

While silver ensembles are well known to form within zeolite cavities under certain conditions, and much larger configurations often form freely on zeolite surfaces, nanodots have not been known to form on zeolite surfaces in concentrations higher than trace levels.

These and other problems with presently known methods for making silver nanodots are exacerbated by the relatively unstable nature of the nanodots. Using presently known methods, silver nanodots produced have only a short shelf life since they tend to quickly agglomerate.

Xenon is present in ambient air at a concentration of 0.087 ppm and is currently derived from air by distillation. Companies specializing in air separation have developed techniques for xenon extraction from air [36-38]. Currently, most of the xenon produced in the world is used in specialized lighting. Other applications include nuclear medicine and laser applications. If it was economical to use, xenon might find widespread application as an anesthetic, having been referred to as ideal [35]. Characteristics of the xenon market and its applications have been reviewed and summarized by Hammarland [39].

Presently, a mixture of krypton and xenon is obtained from an oxygen stream in air distillation. The krypton and xenon are then further separated by cryogenic methods. Due to the high energy requirements of this cryogenic recovery, several alternative processes have been proposed. Certain polymer membranes have shown promise for the separation of xenon from air [40]. Efficient xenon selective adsorbents might allow not only more economical xenon capture from the atmosphere but could conceivably be employed to recapture and recycle xenon from an operating room environment, dramatically cutting its cost per use.

Although the strength of the interaction between silver zeolites and noble gases decreases markedly in the order Xe>Kr>Ar, the sorption affinity for argon is still significant, and some silver zeolites possess the unique property of being measurably selective in adsorbing argon over oxygen. silver mordenite has been reported to manifest at least some argon selectivity (vs. oxygen) [49]. Pressure swing adsorption simulations and experiments were successfully performed for the purification of oxygen (to at least 99.7% purity) from a feed gas comprising of 95% $O_2$ and 5% Ar at 60-90° C. [49]. While silver mordenite appears to be the most widely reported zeolite-based argon selective adsorbent, silver exchanged zeolite X [50], silver exchanged Li—Na-LSX zeolite [51,52], silver exchanged zeolite A [53,54], Y, L, BEA, and ZSM-15 [28] have all been reported to show some degree of argon selectivity (vs. oxygen).

Existing methods for the separation of oxygen and argon are based upon adsorbents that show selectivity for oxygen over argon. However, the separation of argon and oxygen by adsorption-based methods is difficult due to the similar diameter and polarizability of the Ar atoms and $O_2$ molecules. However, molecular sieves and microporous polymers with some degree of selectivity for oxygen are known and have been applied since the 1960s for the chromatographic resolution of Ar, $O_2$, and $N_2$ and other analytical purposes [41-46]. Oxygen (over argon) kinetic selectivity in certain carbon adsorbents has been employed for the production of purified oxygen and argon by pressure swing adsorption (PSA) [47, 48].

Nitrogen also interacts strongly with silver exchanged zeolites. The nitrogen adsorption capacity and isosteric heat of adsorption of fully exchanged zeolite Ag—X was found to be significantly higher than that of Na—X and Li—X [55]. This effect was explained by means of the π-complexation mechanism, which would involve donation of the π-bond electrons of the $N_2$ molecule to the empty s orbital of $Ag^+$, and backdonation of electrons from the d orbital of silver to the empty π-antibonding orbital of $N_{2\,[55]}$. The basic concept for π-complexation was first described by Dewar [56]. The $N_2/O_2$ selectivity of Ag—X zeolite is also reported to be higher than for other cations. This effect has also been explained according to the π-complexation theory. The π-antibonding electrons of the $O_2$ molecule do not allow the back-donation of electrons from the silver d orbitals. The bonding strength of $N_2$ is too strong for practical PSA separations. However, it has been reported that combining the potentials of lithium and silver in hybrid Li—Ag—X zeolite can be superior to Li—X for air separation under certain circumstances. It has also been reported that a small amount of substitution of Ag in Li—X can improve $N_2/O_2$ separation properties [57]. Other silver exchanged zeolites, such as mordenite [58] and zeolite A [54], have been reported to have enhanced $N_2$ capacities and $N_2/O_2$ selectivities compared to materials without silver.

There is also a need in the art for improved adsorbents for noble gases, xenon and argon in particular, which mitigates the disadvantages of the prior art, and there is a need in the art for methods of producing such improved adsorbents.

SUMMARY OF THE INVENTION

In one aspect, the invention comprises a method of forming metal nanodots on a titanosilicate molecular sieve (ETS) zeolite surface. Metal ion-exchange with the ETS zeolite is followed by activating at moderate temperatures. In one embodiment, the ETS zeolite comprises ETS-10 or ETS-4, and materials which are isostructural with ETS-10 or ETS-4.

In another aspect, the invention comprises a composition comprising a plurality of metal nanodots, formed by ion-exchange and subsequent activation on a porous, ion-exchangeable titanosilicate material. The titanosilicate material preferably comprises ETS-10 or ETS-4. In one embodiment, the metal may comprise a transition or noble metal, for example, copper, nickel, palladium or silver.

In one embodiment, silver is a preferred metal. In one embodiment, silver nanodots may form having diameters less than about 100 nm, for example, less than about 50 nm, 30 nm, 20 nm, or 10 nm. In one embodiment, the nanodots are in the order of about 5 to about 15 nm, with a mean of about 10 nm, forming under a wide range of conditions on ETS zeolite surfaces.

The present invention is distinctly different from the well established science of growing metal nanodots or nanowires within a zeolite cage framework, thus producing nanostructures inside the material. In the present invention, unlike in the prior art, the metallic nanodots are surface-accessible on the ETS zeolite support.

Nanostructured silver materials produced in accordance with the present invention may have many useful properties. In one aspect, the invention may comprise a method of selectively adsorbing a noble gas from a gas stream containing the noble gas, using an adsorbent comprising surface accessible metal nanodot ETS. The noble gas may comprise argon, krypton, xenon, or radon. In one embodiment, argon may be separated from an oxygen stream, or xenon may be separated from air, or from a gas stream comprising of nitrogen and oxygen.

In another aspect, the invention may comprise the use of nanodots of silver formed on an ETS material, as an antibacterial or antifungal agent.

Therefore, in one aspect, the invention may comprise a method of forming a metal nanoparticulate material, comprising the steps of:

(a) performing ion-exchange with a solution of the metal ions and an ETS zeolite; and (b) activating the ion-exchanged ETS zeolite.

In another aspect, the invention may comprise an ETS-10 supported metal nanoparticulate material, comprising surface-accessible nanoparticles of metal, having a substantially uniform particle size less than about 100 nm, for example, less than about 50 nm, 30 nm, or 20 nm. In one embodiment, the material may comprise metal nanodots having a diameter in the range of about 5 nm to about 15 nm, and on average about 10 nm.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF PREFERRED EMBODIMENTS

Figure 1:
FIG. 1 shows a TEM image of silver nanoparticles on Ag-ETS-10.

The present invention relates to metallic nanodots formed on ETS zeolites and methods of adsorbing noble gases with such material. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Although consistent terminology has yet to emerge, those skilled in the art generally consider "nanoclusters" to refer to smaller aggregations of less than about 20 atoms. "Nanodots" generally refer to aggregations having a size of about 100 nm or less. "Nanoparticles" are generally considered larger than nanodots, up to about 200 nm in size. In this specification, the term "nanodots" shall be used but is not intended to be a size-limiting nomenclature, and thus may be inclusive of nanoclusters and nanoparticles.

The term "about" shall indicate a range of values 10% above and below the stated value, or preferably +/−5%, or it may indicate the variances inherent in the methods or devices used to measure the value.

As used herein, "ETS zeolite" includes all forms of ETS zeolites including without limitation, ETS-10 and ETS-4. ETS zeolites are described fully in U.S. Pat. No. 5,011,591, Large Pored Crystalline Titanium Molecular Sieve Zeolites, and U.S. Pat. No. 4,938,939, Preparation Of Small-Pored Crystalline Titanium Molecular Sieve Zeolites, and U.S. Pat. No. 4,853,202, Large-Pored Crystalline Titanium Molecular Sieve Zeolites, the entire contents of which are incorporated in their entirety herein by reference. ETS zeolites are a family of stable crystalline titanium silicate molecular sieve zeolites which have a pore size of approximately 4 to 8 Angstrom units and a titania/silica mole ratio in the range from 1.0 to 25. They have a definite and distinct x-ray diffraction pattern and can be identified in terms of mole ratios of oxides. ETS-10 is a molecular sieve zeolite having a crystal structure formed by orthogonal chains of corner sharing $TiO_6$ octahedra which are linked by corner sharing $SiO_4$ tetrahedra. The titania/silica mole ratio is about 2.0 to 25. This layout of structural units generates 12- and 7-membered ring channels which possess a free entrance of about 0.8×0.5 and 0.55×0.15 nm, respectively [22-24]. As used herein, "ETS-10" or "4" includes crystalline titanosilicate zeolitic materials that are isostructural with ETS-10 or ETS-4, as the case may be. Characteristics of both ETS-4 and ETS-10 are reviewed in U.S. Pat. No. 6,464,957, Polymorph-enriched ETS-4, the contents of which are incorporated herein by reference. Without restriction to a theory, suitable ETS materials for the present invention comprise charged, exchangeable octahedral titanium sites.

The term "noble gas" means a chemical element that under standard conditions are substantially odorless, colorless and monoatomic, and that are substantially inert. Noble gases have a full outer shell of valence electrons which contributes to their very low chemical reactivity. Noble gases may include helium, neon, argon, krypton, xenon or radon.

In general terms, in one embodiment, metal nanodots may be formed on an ETS zeolite surface by ion-exchange of the metal cation into the ETS zeolite, followed by an activating step, resulting in the formation of metal nanodots. In one embodiment, the metal is one of silver, copper, nickel, gold or a member of the platinum group. As used herein, a "platinum group" metal is ruthenium, rhodium, palladium, osmium, iridium or platinum. Generally, silver, gold and members of the platinum group are self-reducing. The use of salts of these metals will generally result in the formation of metal nanodots without the imposition of reducing conditions. However, the use of reducing conditions for such metals is preferable, if only to minimize oxidation of the metal. Generally, copper and nickel are reducible and their metal salts will generally result in the formation of metal nanodots upon activation in a reducing atmosphere.

In a preferred embodiment, the metal comprises silver or nickel.

In one embodiment, silver ETS zeolites may be prepared by ion-exchange of ETS zeolites. For example, the ETS zeolites may be exposed to an excess of aqueous silver nitrate under moderate conditions. In one embodiment, ion-exchange takes place at 80° C. with stirring for 1 hour. The material may then be washed and dried. In one embodiment, the above steps are repeated one or more times. The silver ions in the zeolite may then be converted to metallic silver nanodots, supported on the ETS zeolite, by an activation step. In one embodiment, the activation step may simply comprise the step of drying the material at room temperature. In a preferred embodiment, the activation step may comprise annealing the material at an elevated temperature, such as from 75° C. to 500° C. or higher, and preferably between about 75° to about 400° C. The activation step may take from 1 to 4 hours, or longer. In one embodiment, the activation step is performed in a reducing environment.

In one embodiment, the nanodots have a size less than about 100 nm, for example less than about 50 nm, less than about 30 nm or less than about 20 nm. In one embodiment, a substantial majority of the metal nanodots formed have a particle size of less than about 15 nm and greater than about 5 nm, with a mean particle size about 10 nm.

In general, the size of the nanodots appears to be influenced by reducing or oxidizing conditions of the activating step. In one embodiment, the use of reducing conditions results in generally larger nanodot sizes. Conversely, the use of mild oxidizing conditions, such as air, results in generally smaller nanodot sizes.

Without being restricted to a theory, it is believed that the activating process causes the silver ions to migrate to the surface of the ETS zeolite, where they reside as nanodots rather than as large particles or sheets. The silver ions reduce to their metallic state, before or after nanodot formation. Although the exact mechanism of the nanodot formation is not known, and without restriction to a theory, the scale and uniform distribution are likely due to the ability of ETS zeolite surface to attract non-polar species such as a pure metal. As a result, pure metals tend to stick to the surface of the ETS zeolite surface.

In a preferred embodiment, the ETS zeolite comprises ETS-10, and silver is the metal used to form the metallic nanodots in an Ag-ETS-10 complex.

Silver nanodot ETS zeolites such as Ag-ETS-10 may have many possible uses which exploit the macro and nano properties of the metallic element. In one embodiment of a silver nanoparticulate material, it may be used as a novel anti-microbial agent. Ag-ETS may incorporated into bandages, wound dressings or the like, or incorporated into solutions, creams or ointments, or the like, to be used to prevent or treat microbial infections. The formulation of anti-microbial solutions, creams, ointments, coatings are well-known to those skilled in the art and need not be further described herein.

While it is known that, in general, silver exchanged zeolites exhibit unusual adsorption properties, especially toward the noble gases, and Ar, Kr, Xe or Rn in particular, the Ag-ETS zeolites of the present invention surprisingly provide more selective or stronger adsorption properties than prior art silver zeolites. Therefore, in one aspect, the invention may comprise the use of Ag-ETS zeolites to selectively adsorb a noble gas from a gaseous mixture or stream. The noble gas may be a member of group 18 of the periodic table, and may comprise one or more of Ar, Kr, Xe or Rn.

Without restriction to a theory, the nature of noble gas adsorption in silver zeolites generally may be related to the directional properties given by the d orbitals of silver ions [1]. $Ag^+$ ions in silver zeolites react, upon heating, to generate clusters with a wide range of compositions including metal nanoensembles and groupings which may be composed of a combination of silver atom clusters and ions. The clusters can occupy different sites in the zeolitic structure [25]. This variability in composition and location of the clusters results in materials which can express many different colors (from white or light yellow to dark gray), dependent upon the state of the silver and its thermal history [25-27].

Enhanced interaction between xenon and silver exchanged zeolites X and Y has been reported, including xenon adsorption isotherms and xenon NMR [28-30]. The initial isosteric heat of xenon adsorption for silver zeolites is uniformly higher than for their sodium analogs, and a substantial displacement of the chemical shift has been observed in the $^{129}Xe$ NMR spectrums with silver present. The adsorption capacity of xenon and krypton on silver mordenite as well as 5A zeolite and activated carbon, especially at very low pressures [31].

It is believed that xenon is adsorbed more strongly in the silver-exchanged zeolites than in their sodium analogs, based on studies of xenon adsorption and $^{129}Xe$ NMR in silver-exchanged X and Y zeolites [32, 33]. This stronger interaction was also seen in the displacement of the chemical shifts of $^{129}Xe$ adsorbed on silver zeolites when compared to those of the sodium starting materials. This was qualitatively explained by specific interactions of xenon with the silver cations in the super-cages of the zeolites. It has also reported that the initial isosteric heat of adsorption of xenon was 31 kJ/mol in silver-exchanged zeolite Y compared to 18.5 kJ/mol in the sodium form [34].

In one aspect of the invention, silver nanodot ETS of the present invention may be used as an adsorbent for xenon, as demonstrated below with both isothermal and chromatographic data. Therefore, silver nanodot ETS may be used for xenon recovery and purification. In one embodiment, the silver nanodot ETS is placed in a gas flow which comprises xenon to selectively adsorb the xenon. Once adsorbed, the xenon may then be released by heating the adsorbent in a full or partial vacuum. In one embodiment, xenon adsorbed on Ag-ETS-10 can be completely removed by applying a vacuum at 150° C.

In another embodiment, silver nanodot ETS zeolites are selective for argon over oxygen. Therefore, in one embodiment, silver nanodot ETS zeolites may be used to generate substantially pure oxygen from a gas stream comprising oxygen and argon. The material also demonstrates selectivity for nitrogen as demonstrated below.

From chromatographic and volumetric isotherm measurements, silver nanodot ETS demonstrates adsorptive selectivity for argon over oxygen at 30° C. over a wide range of pressures. This selectivity increases with decreasing pressure where it reaches 1.49 at the Henry's law limit. Therefore, silver nanodot ETS may be used as an adsorbent for the production of high purity oxygen (>99%) from a previously enriched oxygen stream containing argon. An enriched oxygen stream from PSA air separation contains approximately 95% $O_2$ and 5% Ar. With its substantially higher Ar/$O_2$ selectivity at low argon partial pressures, silver nanodot ETS is a suitable material to improve $O_2$ generation under these conditions by selectively adsorbing argon from a mixed stream of oxygen and argon.

EXAMPLES

The following examples are provided to exemplify specific embodiments of the invention, and are not intended to limit the claimed invention in any manner, unless specifically recited as a claim limitation.

Example 1

Production of Ag-ETS-10

ETS-10 was synthesized under hydrothermal conditions as reported by Kuznicki in U.S. Pat. No. 5,011,591. The ETS-10 adsorbent was ion exchanged by adding 5 g of ETS-10 to 10 g of silver nitrate (Fisher, USP) in 50 g of deionized water. The mixture was heated to 80° C. for a period of 1 h. The silver treated material was filtered, washed with deionized water and the exchange procedure was repeated twice (for a total of three exchanges). The silver exchanged ETS-10 was dried at 80° C. Elemental analysis indicated essentially quantitative silver exchanged with Ag constituting slightly more than 30% of the finished material (by weight).

Example 2

Adsorption of Xenon—Experimental Parameters

Two adsorbents were examined, Na-ETS-10 and its silver exchanged counterpart Ag-ETS-10. Inverse gas chromatography data were obtained on a Shimadzu GC 14-B apparatus. Adsorbents were packed into columns and pretreated under helium flow at 250° C. over night. Test gas samples were injected into the columns at pre-chosen temperature intervals. Corrected retention times for each gas at the test temperature are reported in Table 1 below.

TABLE 1

Chromatographic Data for Xenon and Air Traversing ETS-10
Based Adsorbent Columns at Various Temperatures and Projected
Selectivities (α) of Xe/air ($N_2$) at 25° C.

| sample | T [° C.] | retention time [min] air ($N_2$) | Xe | α [mol/mol] | $q_{st}$ [kJ/mol] air ($N_2$) | Xe | α (25° C.) |
|---|---|---|---|---|---|---|---|
| Ag-ETS-10 | 200 | 0.53 | 39.29 | 138 | 32.1 | 52.5 | 2903 |
|  | 225 | 0.45 | 21.28 | 107 |  |  |  |
|  | 250 | 0.39 | 12.18 | 85 |  |  |  |
| Na-ETS-10 | 30 | 1.78 | 26.84 | 18 | 22.8 | 27.5 | 18.5 |
|  | 50 | 1.20 | 14.70 | 16 |  |  |  |
|  | 70 | 0.88 | 9.40 | 16 |  |  |  |
|  | 100 | 0.62 | 4.45 | 13 |  |  |  |

Mathematical analysis of the GC data using the Clausius-Clapeyron equation [59] was performed, using Henry's law constants, to project xenon/air ($N_2$) selectivities to room temperature. These projections were then compared to adsorption isotherms as described below.

Adsorption isotherms for Xe, $N_2$, and $O_2$ were obtained by gravimetric analysis using a Rubotherm magnetic suspension balance system (accuracy of ±0.1 ug) constructed to our specifications by VTI Corp. of Hialeah, Fla. Samples were activated at 150° C. under a vacuum of greater than $10^{-4}$ Torr for a period of 6 h.

Example 3

Adsorption of Xenon—Results

Xenon adsorption isotherms were measured at various temperature increments (25, 60, 100, and 150° C.), and these isotherms were used to calculate isosteric heats of adsorption ($qs_1$) as a function of adsorbate loading by plotting ln p vs 1 IT [60].

Figure 2:
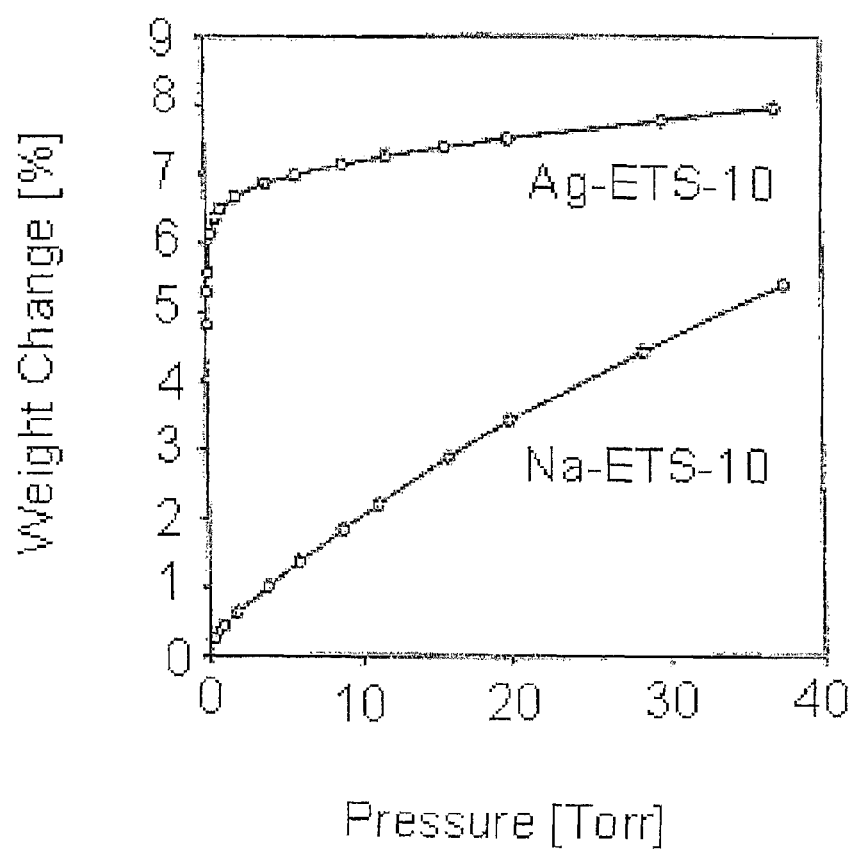
FIG. 2 is a graph showing xenon adsorption isotherms at 25° C. for raw (Na-ETS-10) and modified (Ag-ETS-10) samples.

On Na-ETS-10, xenon adsorption at 25° C. is nearly linear with pressure as shown in FIG. 2. However, silver exchange dramatically changes adsorption behavior, generating a steep isotherm which reaches 6% weight loading by 0.5 Torr at 25° C.

Figure 3A:
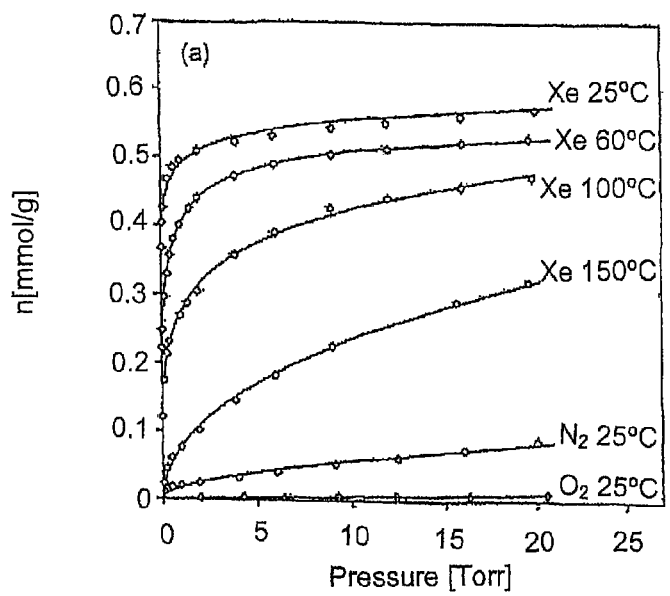
FIG. 3(a) is a graph showing xenon adsorption isotherms at various temperatures with $O_2$ and $N_2$ isotherms at 25° C. included for comparison.
Figure 3B:
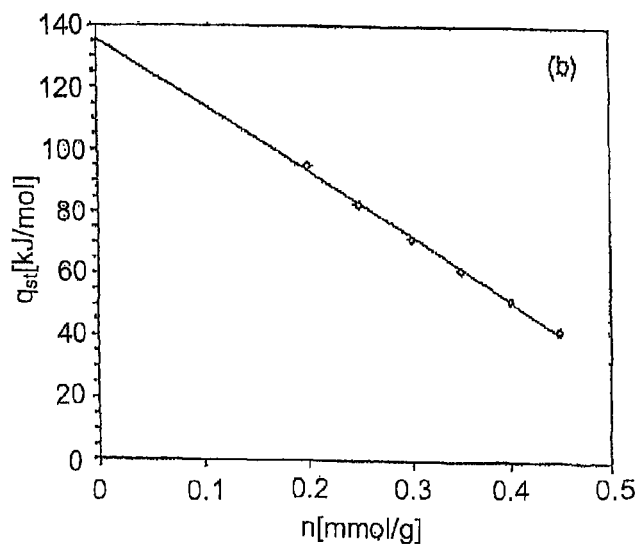
FIG. 3(b) is a graph showing isosteric heats of xenon adsorption at various loadings.

When low-pressure xenon isotherms are measured at temperatures between 25 and 150° C. (FIG. 3a), adsorption is substantial, even at elevated temperatures. Comparative nitrogen and oxygen isotherms (FIG. 3a) infer substantial selectivity for the removal of xenon from air. Using these isotherms, isosteric heats of adsorption for xenon at various adsorbate loadings were calculated (FIG. 3b). In the range of adsorbent loadings available, the values of $q_{st}$ varied with loading from 40 to greater than 90 kJ/mol adsorbed. Linear extrapolation to zero loading gives a projected value of approximately 136 kJ/mol for the limiting isosteric heat of adsorption. If correct, this is of the same magnitude as reported for Xe—F bond energies in Xe—$F_6$ and Xe—F4 [61].

This interaction is much stronger than previously reported for Ag loaded classical zeolites such as X and Y [33,34]. This strong interaction cannot be rationalized by classical zeolite cation-adsorbate interactions or interactions with the zeolite framework. It is known that silver cations in certain exchanged zeolites can be reduced to metal nanoparticles at temperatures as low as 150° C. [62]. TEM images show the formation of what appears to be silver nanoparticles on the ETS-10 surfaces (FIG. 1). Nanostructured silver might be expected to maximize silver's interaction energies with potential sorbates including xenon. The activated Ag-ETS-10 also lacks the yellow coloration generally associated with $Ag^+$ ions in molecular sieves [63, 64, 65]. Without being bound to a theory, we presume the strong binding with xenon comes from its interaction with the silver nanodots.

The heat of adsorption calculated from isotherm modeling may appear to be unrealistically high for a reversible physisorption process. However, both the shape of the isotherms and the projected limiting heat of adsorption are strongly reminiscent of a polar molecule such as water on a classical zeolite desiccant (such as zeolite X or zeolite A). Such isotherms and isosteric heat plots are usually associated with a finite population of very strong adsorption sites coupled with a large surface at lower binding energy. Zeolite desiccants form the basis of many regenerable (reversible) drying processes. Xenon adsorbed on Ag-ETS-10 can be completely removed by applying a vacuum at 150° C.

Figure 4:
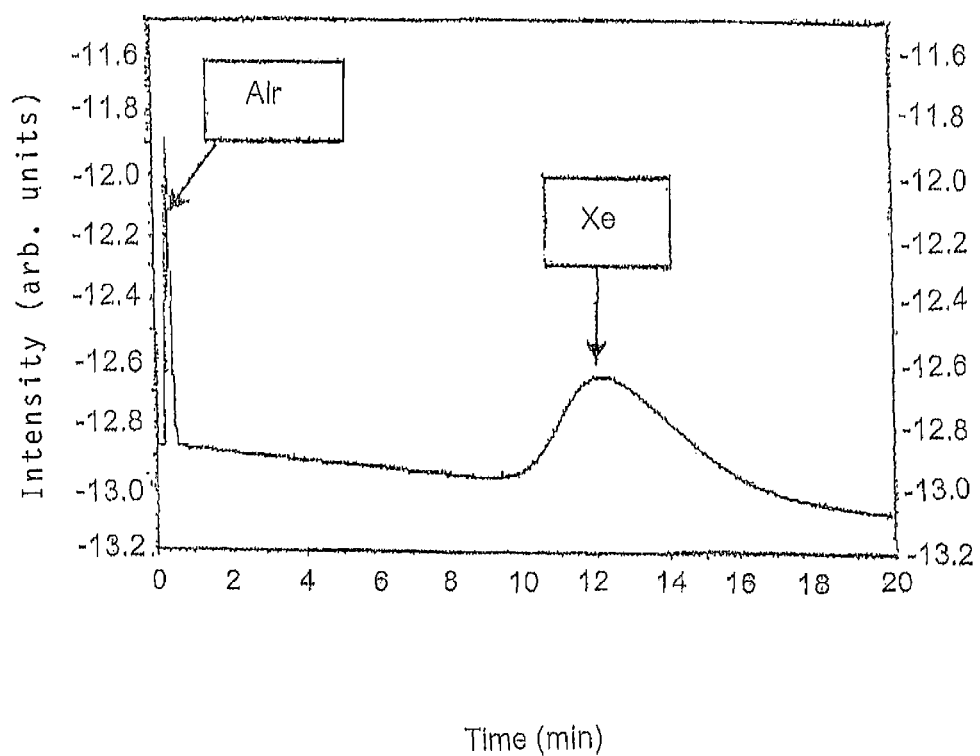
FIG. 4 shows a gas chromatographic profile for xenon/air separation at 250° C. on Ag-ETS-10.

Xenon interacts with Ag-ETS-10 so strongly that inverse gas chromatography experiments required elevated temperatures for practical run times. FIG. 4 depicts the GC printout of a 50-50 mixture of xenon and air injected in a 10"×¼" column of Ag-ETS-10 at 250° C. under 30 $cm^3$/min flow of helium. Air traverses the column quickly, essentially in the time of an inert gas, whereas xenon shows substantial retention, even at 250° C. Both xenon and air rapidly traverse in a Na-ETS-10 column under these conditions. Table 1 lists the chromatographic data for Ag-ETS-10 in the temperature regime of 200-250° C. and Na-ETS-10 from 30 to 100° C. Projections of these data to room temperature (25° C.) indicate a xenon/air ($N_2$) selectivity of approximately 18 for Na-ETS-10 which rises to nearly 3000 in the silver form. Such extremely selective xenon adsorbents might be employed to effectively scrub an operating room's air to recover (and recycle) valuable xenon anesthetics.

The indicated heat of adsorption for xenon from the inverse gas chromatography experiments (at 52.5 kJ/mol) is substantially less than the projected 130+ kJ/mol from adsorption isotherms. We do not know whether this is due to our adsorption modeling being incorrect for this new system or if GC data are not representative of the Henry's law regime for such a strong adsorbent. Both the relative symmetry of the xenon peaks and their small variations in retention with injection size support the GC binding energies while adsorption isotherms qualitatively and quantitatively support the higher value. Irrespective, both techniques indicate unprecedented selectivity for the adsorption of xenon from air ($N_2$). It must be noted that a full cc injection of xenon takes over 12 min to pass through a column containing only about 3 g of adsorbent at 250° C. and 30 $cm^3$/min carrier flow. Projected Henry's law constants from the chromatographic data indicate that this passage time would approach 1 month at room temperature.

Example 4

Argon Adsorption—Experimental Parameters

A comparative study was done between Ag-mordenite and Ag-ETS-10. In order to obtain Ag-mordenite, hydrogen mordenite (from Zeolyst Corp.) was silver exchanged in a manner similar to that described for ETS-10. With its inherently lower exchange capacity, the silver loading on the mordenite was found to be approximately 8% (by weight) by elemental analysis.

Inverse gas chromatography experiments were performed using a Varian CP 3800 gas chromatograph (GC). Test adsorbents were packed into 10" long, ¼" OD copper columns. Typical columns contained approximately 3 g of test adsorbent. The columns were installed in the Varian CP 3800 GC and were treated at 350° C. for 16 h under 30 ml/min helium carrier flow. The test gas samples constituted 1 cc injection of Ar, $O_2$, and 50-50% mixtures of $O_2$—Ar and were performed at 30° C. with 30 ml/min helium carrier flow.

Low pressure (up to 120 kPa) nitrogen, oxygen, and argon adsorption isotherms were measured at 30° C. in a Micromeritics (ASAP 2010) volumetric adsorption system. Test samples were dried (150° C. for Ag-ETS-10 and 350° C. for Ag-mordenite) for 6 h under a vacuum of greater than $10^{-4}$ Torr. Adsorption isotherms were fitted to the classical Langmuir equation:

$$n = \frac{n_m \cdot K_L \cdot p}{1 + K_L \cdot p},$$

Where n is the amount adsorbed (mmol $g^{-1}$) at the pressure p (kPa), and $n_m$ and $K_L$ are the fitting parameters. According to the Langmuir model, $n_m$ is interpreted as the mono-layer coverage (mmol/g), and the product $n_m \cdot K_L$, (mmol $g^{-1}$ $kPa^{-1}$) equals the Henry's law constant at low loading, when p→+0. The selectivity (a) was calculated from the pure gas Langmuir isotherms as:

$$\alpha(A/B) = \frac{K_A}{K_B},$$

Where α (A/B) is the selectivity of gas over gas 13 expected at low loadings and expressed as the ratio of their respective Henry's law constants $K_A$ and $K_B$ (K=n, , , $\cdot K_L$).

Example 5

Argon Adsorption—Results

Color changes were noted for both Ag-ETS-10 and Ag-mordenite during activation. Ag-ETS-10 is initially light brown and becomes dark gray after heating to 150° C. in vacuum. Ag-mordenite changes from a light greenish yellow to a light gray with activation at 350° C. The color changes infer a change in the state of silver during activation, presumed to be partial or total reduction to metal. Mordenite required the higher temperature for complete activation.

Figure 5A:
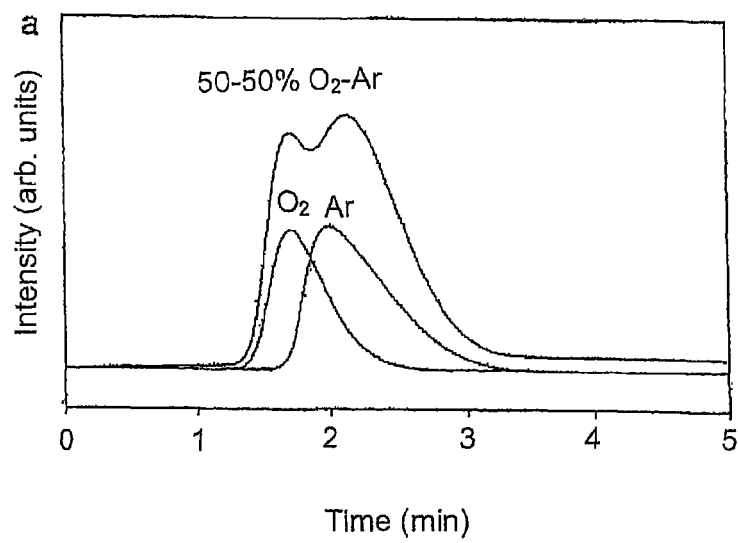
FIG. 5(a) shows a gas chromatographic profile obtained at 30° C. with 30 ml/min of helium carrier flow for Ar, $O_2$ and a 50%-50% mixture of Ar—$O_2$ on Ag-ETS-10.
Figure 5B:
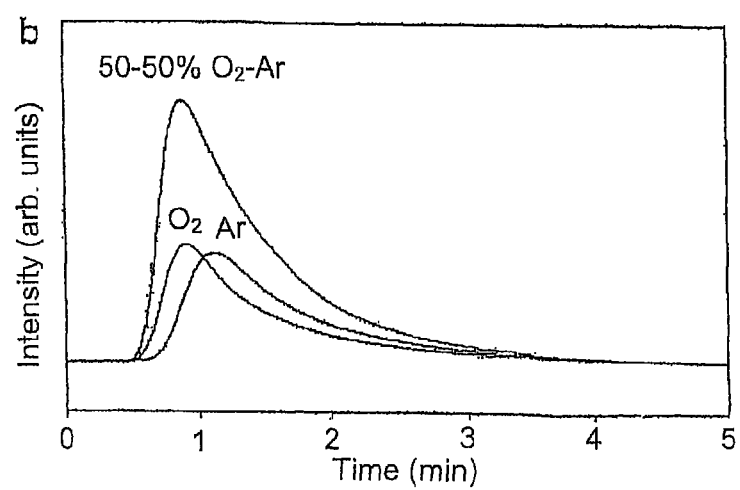
FIG. 5(b) shows a gas chromatographic profile obtained at 30° C. with 30 ml/min of helium carrier flow for Ar, $O_2$ and a 50%-50% mixture of Ar—$O_2$ on Ag-mordenite.

FIGS. 5a and 5b show gas chromatographic profiles for Ag-ETS-10 and Ag-mordenite with injections of both a 50-50% mixture of $O_2$—Ar and injections of the pure gases. The retention times for pure argon are larger than for pure oxygen in both Ag-ETS-10 and Ag-mordenite, indicating an affinity for argon over oxygen, although chromatographic splitting is much more obvious for Ag-ETS-10 when the mixed gases are injected.

Figure 6A:
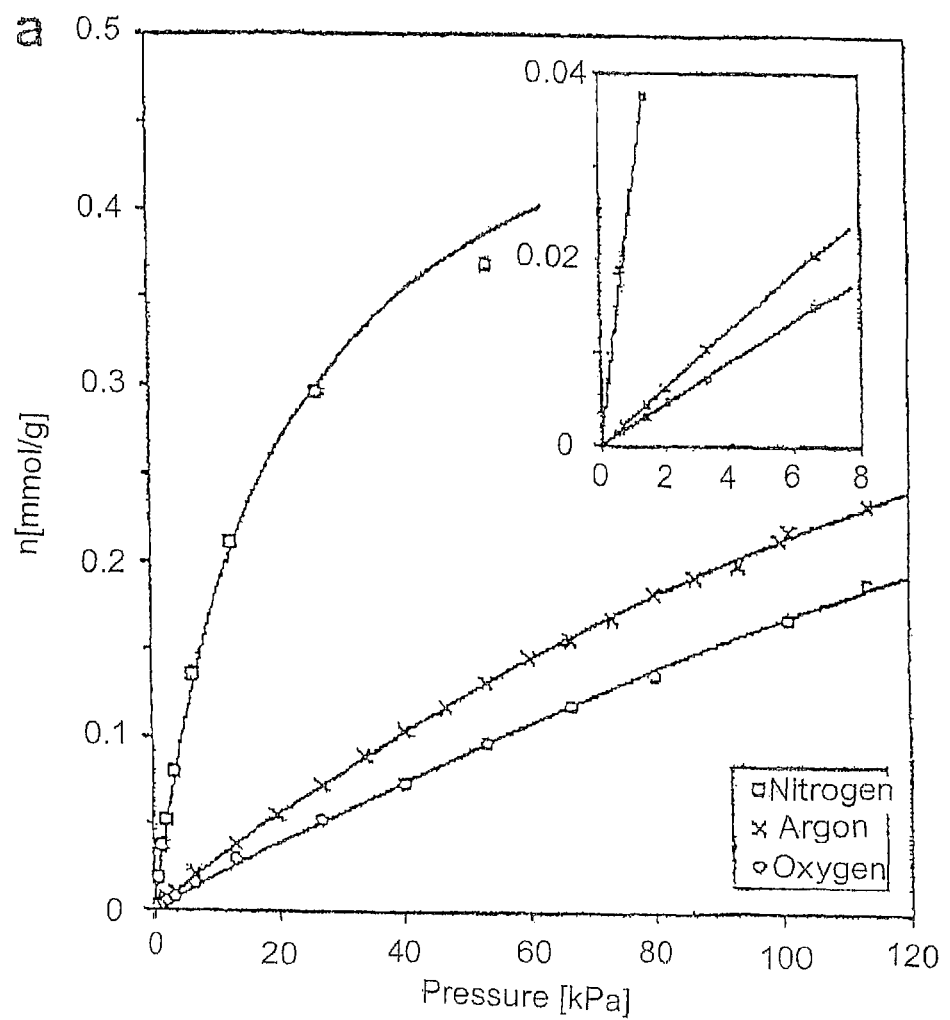
FIG. 6(a) is a graph showing nitrogen, argon, and oxygen adsorption isotherms at 30° C. on Ag-ETS-10 with an insert to expand the lower pressure regime.
Figure 6B:
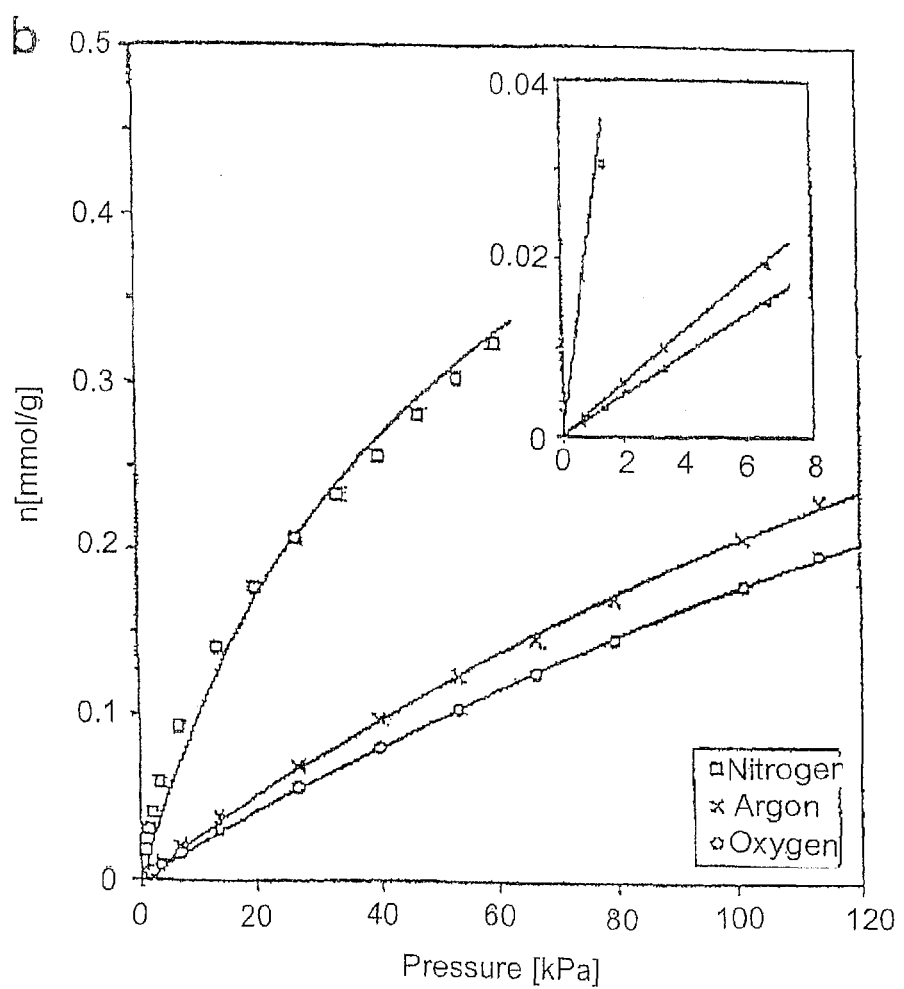
FIG. 6(b) is a graph showing nitrogen, argon, and oxygen adsorption isotherms at 30° C. on Ag-mordenite with an insert to expand the lower pressure regime.

FIGS. 6a and 6b show nitrogen, argon, and oxygen adsorption isotherms for Ag-ETS-10 and Ag-mordenite together with their Langmuir fitting curves up to a pressure of 120 kPa. A blow-up of isotherm data at lower pressures (up to 8 kPa) is included as an insert. Up to 120 kPa, all experimental isotherms fit the Langmuir model well. The parameters of these) Langmuir isotherms are listed in Table 2, together with their standard deviations (σ):

$$\sigma = \frac{\sum (n_{exp} - n_{calc})}{N - m},$$

Where $n_{exp}$ is the experimentally measured adsorption (mmol $g^{-1}$) at pressure p (kPa) and $n_{calc}$ is the adsorption calculated from the Langmuir equation at the same pressure. N is the number of experimental points taken and m is the number of fitting parameters (2 for the Langmuir equation).

| Langmuir parameters for the adsorption data in the range of 0-120 kPa | | | |
|---|---|---|---|
| Langmuir (0-120 kPa) | | Ag-ETS-10 | Ag-mordenite |
| Nitrogen | $n_m$ (mmol $g^{-1}$) | 0.53865 | 0.62092 |
| | $K_L \cdot n_m$ (mmol $kPa^{-1}$ $g^{-1}$) | 0.02546 | 0.01171 |
| | $\sigma \cdot 10^3$ | 0.108 | 0.148 |
| Argon | $n_m$ (mmol $g^{-1}$) | 0.73262 | 0.84651 |
| | $K_L \cdot n_m$ (mmol $kPa^{-1}$ $g^{-1}$) | 0.00302 | 0.00272 |
| | $\sigma \cdot 10^3$ | 0.002 | 0.005 |
| Oxygen | $n_m$ (mmol $g^{-1}$) | 0.98753 | 0.93305 |
| | $K_L \cdot n_m$ (mmol $kPa^{-1}$ $g^{-1}$) | 0.00202 | 0.00218 |
| | $\sigma \cdot 10^3$ | 0.004 | 0.001 |
| | α ($N_2$/Ar) | 8.44 | 4.30 |
| | α ($N_2$/$O_2$) | 12.58 | 5.36 |
| | α (Ar/$O_2$) | 1.49 | 1.25 |

The calculated Langmuir adsorption isotherms were used to predict the selectivity of Ag-ETS-10 and Ag-mordenite for nitrogen, argon, and oxygen. The resulting selectivities for the Henry's law limiting region are included in Table 2. Both Ag-ETS-10 and Ag-mordenite demonstrate some selectivity for argon over oxygen at atmospheric pressure, and this is magnified at low pressure, especially in the case of Ag-ETS-10, which reaches a selectivity of 1.49 at its limit. Both materials show strong selectivity for nitrogen over oxygen and argon at low pressures, especially Ag-ETS-10 where the limiting $N_2/O_2$ selectivity exceeds 10. Considering that Ag-ETS-10 is approximately twice as dense as Ag-mordenite, differences in actual bed selectivities would probably be greater than indicated by the isotherms.

From chromatographic, volumetric and gravimetric isotherm measurements, both Ag-ETS-10 and Ag-mordenite demonstrate adsorptive selectivity for argon over oxygen at 30° C. over a wide range of pressures. This selectivity increases with decreasing pressure, especially in the case of Ag-ETS-10, where it reaches 1.49 at the Henry's law limit. Ag-mordenite has been proposed as useful adsorbent for the production of high purity oxygen (>99%) from a previously enriched oxygen stream (from PSA air separation) containing approximately 95% $O_2$ and 5% Ar. Ag-ETS-10 shows substantially higher Ar/$O_2$ selectivity at low argon partial pressures.

REFERENCES

The following references are referred to in square brackets above, and, where permitted, the entire contents of these references are incorporated herein as if reproduced in their entirety.

[1] R. Jin, Y. Cao, E. Hao, G. C. Metraux, G. C. Schatz, C. A. Mirkin, Nature 425 (2003) 287.
[2] R. Jin, Y. Cao, C. A. Mirkin, K. L. Kelly, G. C. Schatz, J. G. Zheng, Science 294 (2001) 1901.
[3] A. Callegari, D. Tonti, M. Chergui, Nano Lett. 3 (2003) 1565,
[4] Y. Sun, B. Mayers, Y. Xia, Nano Lett. 3 (2003) 675.
[5] Y. Sun, Y. Xia, Adv. Mater. 15 (2003) 695.

[6] S. Chen, D. L. Carroll, Nano Lett. 2 (2002) 1003.
[7] Y. Zhou, C. Y. Wang, Y. R. Zhu, Z. Y. Chen, Chem. Mater. 11 (1999) 2310.
[8] M. J. Edmondson, W. Zhuo, S. A. Sieber, I. P. Jones, I. Gameson, P. A. Anderson, P. P. Edwards, Adv. Mater. 13 (2001) 1608.
[9] C. R. Li, X. N. Zhang, Z. Zhang, Mater. Lett. 58 (2004) 27.
[10] L. M. Worboys, P. A. Anderson, in: E. van Steen, L. H. Callanan, M. Claeys (Eds.), Recent Advances in the Science and Technology of Zeolites and Related Materials, Parts A, B, C, Studies in Surface Science and Catalysis, vol. 154, 2004, p. 931.
[11] M. Tsapatsis, AIChE J. 48 (2002) 654.
[12] R. Strohal, M. Schelling, M. Takacs, W, Jurecka, U. Gruber, F. Offner, J. Hospital Infect. 60 (2005) 226.
[13] R. E. Burrell, L. R. Morris, P. S. Apte, S. B. Sant, K. S. Gill, U.S. Pat. No. 5,837,275 (1998).
[14] G. S. Metraux, C. A. Mirkin, Adv. Mater. 17 (2005) 412.
[15] L. R. Gellens, W. J. Mortier, J. B. Uytterhoeven, Zeolites 1 (1981) 85.
[16] V. S. Gurin, V. P. Petranovskii, N. E. Bogdanchikova, Mater. Sci. Eng. C 19 (2002) 327.
[17] V. S. Gurin, V. P. Petranovskii, N. E. Bogdanchikova, Mater. Sci. Eng. C 23 (2003) 81.
[18] V. S. Gurin, V. P. Petranovskii, M.-A. Hernandez, N. E. Bogdanchikova, A. A. Alexeenko, Mater. Sci, Eng. A 391 (2005) 71.
[19] G. Bagnasco, P. Ciamgelli, E. Czaran, J. Rapp, G. Russo, in: P. A. Jacobs, D. Forschungsgemeinschaft (Eds.), Metal Microstructures in Zeolites, Elsevier, Amsterdam, 1982.
[20] S. J. Cho, J. E. Yie, R. Ryoo, Catal. Lett. 71 (2001) 163.
[21] V. Alt, T. Bechert, P. Steinrucke, M. Wagener, P. Seidel, E. Dingeldein, E. Domann, R. Schnettler, Biomaterials 25 (2004) 4383.
[22] M. W. Anderson, O. Terasaki, T. Oshuna, A. Philippou, S. P. Mackay, A. Ferreira. J. Rocha and S, Lidin, *Nature* (London)1994, 367, 347.
[23] M. W. Anderson, O. Terasaki, T. Oshuna, P. J. O. Malley, A. Philippou, S. P. Mackay, A. Ferreira. J. Rocha and S. Lidin *Philos. Mag. B.,* 1995, 71, 813.
[24] J. M. Thomas, M. W. Anderson, P. A. Wright and J. Rocha *J. Phys. Chem.,* 1996, 100, 449.
[25] T. Sun, K. Seff, Chem. Rev. 94 (1994) 857.
[26] N. D. Hutson, B. A. Reisner, R. T. Yang, B. H. Toby, Chem. Mater. 12 (2000) 3020.
[27] J. Sebastian, R. V. Jasra, Ind. Eng. Chem. Res. 44 (2005) 8014.
[28] R. Grosse, R. Burmeister, B. Boddenberg, A. Gedeon, J. Fraissard, J. Phys. Chem. 95 (1991) 2443
[29] R. Grosse, A. Gedeon, J. Watermann, J. Fraissard, B. Boddenberg, Zeolites 12 (1992) 909.
[30] J. Watermann, B. Boddenberg, Zeolites 13 (1993) 427.
[31] K. Munakata, S. Kanjo, S. Yamatsuki, A. Koga, D. Ianovski, J. Nucl. Sci. Technol. 40 (2003) 695.
[32] Grosse, R.; Burmeister, R.; Boddenberg, B.; Gedeon, A.; Fraissard, *J. J. Phys. Chem.* 1991, 95, 2443.
[33] Grosse, R.; Gedeon, A.; Watermann, J.; Fraissard, J.; Boddenberg, B. *Zeolites* 1992, 12, 909.
[34] Watermann, J.; Boddenberg, B. *Zeolites* 1993, 13, 427.
[35] Lynch. C.; Baum, J.; Tenbrinck, R. *Anesthesiology* 2000, 92, 865.
[36] Shino, M.; Takano, H.; Nakata J.; Noro, K. Production process of xenon. U.S. Pat. No. 4,874,592, 1989.
[37] Cheung, H.; Couche, M. R.; Dray, J. R. Xenon production system. U.S. Pat. No. 5,069,698, 1991.
[38] Agrawal, R.; Farrell, B. E. Cryogenic production of krypton and xenon from air. U.S. Pat. No. 5,122,173, 1992.
[39] Hammarland, *N. Nucl. Instrumn. Methods Phys. Res., Sect. A* 1992, 316, 83.
[40] Jensvold, J. A.; Jeanes, T. O. Membrane for separation of xenon from oxygen and nitrogen and method for using same. U.S. Pat. No. 6,168,649, 2001.
[41] E. W. Lard, R. C. Horn, Anal. Chem. 32 (1960) 878.
[42] K. Jones, P. Halford, Nature 202 (4936) (1964) 1003.
[43] J. A. J. Walker, Nature 209 (5019) (1966) 197.
[44] G. E. Pollock, D. O'Hara, J. Chromatogr. Sci. 22 (1984) 343.
[45] G. E. Pollock, J. Chromatogr. Sci. 24 (1986) 173.
[46] P. J. Maroulis, C. G. Coe, Anal. Chem. 61 (1989) 1112.
[47] S. U. Rege, R. T. Yang, Adsorption 6 (2000) 15.
[48] X. Jin, A. Malek, S. Farooq, Ind. Eng. Chem. Res. 45 (2006) 5775.
[49] K. S. Knaebel, A. Kandybin, U.S. Pat. No. 5,226,933, 1993.
[50] A. I. Kandybin, R. A. Anderson, D. L. Reichley, U.S. Pat. No. 5,470,378, 1995.
[51] R. L. Chiang, R. D. Whitley, J. E. Ostroski, D. P. Dee, U.S. Pat. No. 6,432,170 B1, 2002.
[52] D. P. Dee, R. L. Chiang, E. J. Miller, R. D. Whitley, U.S. Pat. No. 6,544,318 B2, 2003.
[53] J. Sebastian, R. V. Jasra, U.S. Pat. No. 6,572,838 B1, 2003.
[54] J. Sebastian, R. V. Jasra, Chem. Commun. (2003) 268.
[55] R. T. Yang, Y. D. Chen, J. D. Peck, N. Chen, Ind. Eng. Chem. Res. 35 (1996) 3093.
[56] M. J. S. Dewar, Bull. Soc. Chim. Fr. (1951) C71.
[57] N. D. Hutson, S. U. Rege, R. T. Yang, AIChE J. 45 (1999) 714.
[58] I. Salla, P. Salagre, Y. Cesteros, F. Medina, J. E. Sueiras, J. Phys. Chem. B 108 (2004) 5359.
[59] Diaz, E.; Ordfiez, S.; Vega, A.; Coca, J. *Thermochim. Acta* 2005, 434, 9.
[60] Zangwill, A. Physics at Surfaces; Cambridge University Press: Cambridge, 1988; pp 192-194.
[61] Huheey, J. E. *Inorganic chemistry,* 3rd ed.; Harper & Row: New York, 1983; Appendix E.
[62] Kuznicki, S. M.; Kelly, D. J. A.; Bian, J.; Lin, C. C. H.; Liu, Y.; Chen, J.; Mitlin, D.; Xu, Z. *Micropor. Mesopor. Mater*. in press.
[63] Sun, T.; Seff, K. *Chem. Rev.* 1994, 94, 857.
[64] Hutson, N, D.; Reisner, B. A.; Yang, R. T.; Toby, B. H. *Chem. Mater.* 2000, 12, 3020.
[65] Sebastian, J.; Jasra, R. V. *Ind. Eng. Chem. Res.* 2005, 44, 8014.

What is claimed:

1. A method of selectively adsorbing a noble gas from a gas stream containing the noble gas, comprising the step of passing the gas stream over an adsorbent material comprising a porous material having ion-exchangeable octahedral titanium sites and metal nanodots disposed on a surface of the material that is external to the pores of the material.

2. The method of claim 1 wherein the material comprises ETS-4 or ETS-10, or a material isostructural with ETS-4 or ETS-10.

3. The method of claim 1 wherein the metal comprises silver, copper, nickel, gold or a member of the platinum group.

4. The method of claim 3 wherein the metal comprises silver.

5. The method of claim 1 wherein the metal nanodots have a particle size less than about 100 nm.

6. The method of claim 5 wherein the nanodots have a particle size less than about 50 nm.

7. The method of claim 6 wherein the nanodots have a particle size less than about 15 nm and greater than about 5 nm.

8. The material method of claim 2 wherein the ETS material comprises ETS-10, or a material isostructural with ETS-10.

9. The method of claim 1 wherein the noble gas comprises argon, xenon, krypton or radon.

10. The method of claim 9 which occurs at a temperature between 20° C. and 150° C.

11. The method of claim 1 further comprising the step of releasing the noble gas from the adsorbent by heating the adsorbent under a reduced pressure.

12. The method of claim 11 wherein the noble gas is released from the adsorbent by heating to about 150° under a full or partial vacuum.

13. The method of claim 9 wherein the noble gas comprises argon.

14. The method of claim 9 wherein the noble gas comprises xenon.

15. The method of claim 13 wherein the method comprises a method of producing substantially pure oxygen from a gas stream comprising oxygen and argon.

16. The method of claim 15 wherein the method comprises a method of producing substantially pure oxygen from air.

* * * * *